United States Patent [19]
Heacock

[11] Patent Number: 5,526,189
[45] Date of Patent: Jun. 11, 1996

[54] LENS FOR OBSERVATION OF THE INTERIOR OF THE EYE

[76] Inventor: Gregory L. Heacock, 331 NE. 3rd Pl., Camas, Wash. 98607

[21] Appl. No.: 329,216

[22] Filed: Oct. 26, 1994

[51] Int. Cl.$^6$ ..................................................... G02B 3/08
[52] U.S. Cl. ............................................ 359/718; 351/205
[58] Field of Search .............................. 351/205; 359/708, 359/718, 719

[56] References Cited

U.S. PATENT DOCUMENTS

| | | | |
|---|---|---|---|
| 5,333,017 | 7/1994 | Volk | 351/205 |
| 5,430,506 | 7/1995 | Volk | 359/708 |

*Primary Examiner*—Scott J. Sugarman
*Attorney, Agent, or Firm*—McAndrews, Held & Malloy, Ltd.

[57] ABSTRACT

A lens allows a wide field of view of the interior of a patient's eye to be observed without requiring the eye to be dilated. The lens is nonsymmetric and formed of an optically transparent material having two nonspherical surfaces. The surface of the lens facing the patient's eye has a curvature sufficient to bend the image forming rays emanating from the undilated eye towards a second surface which has a curvature sufficient to form the rays into a planar, real, inverted image of the fundus with a field of view of greater than 60° and a ratio of the effective focal length of the lens to the lens diameter that is less than 0.5.

13 Claims, 1 Drawing Sheet

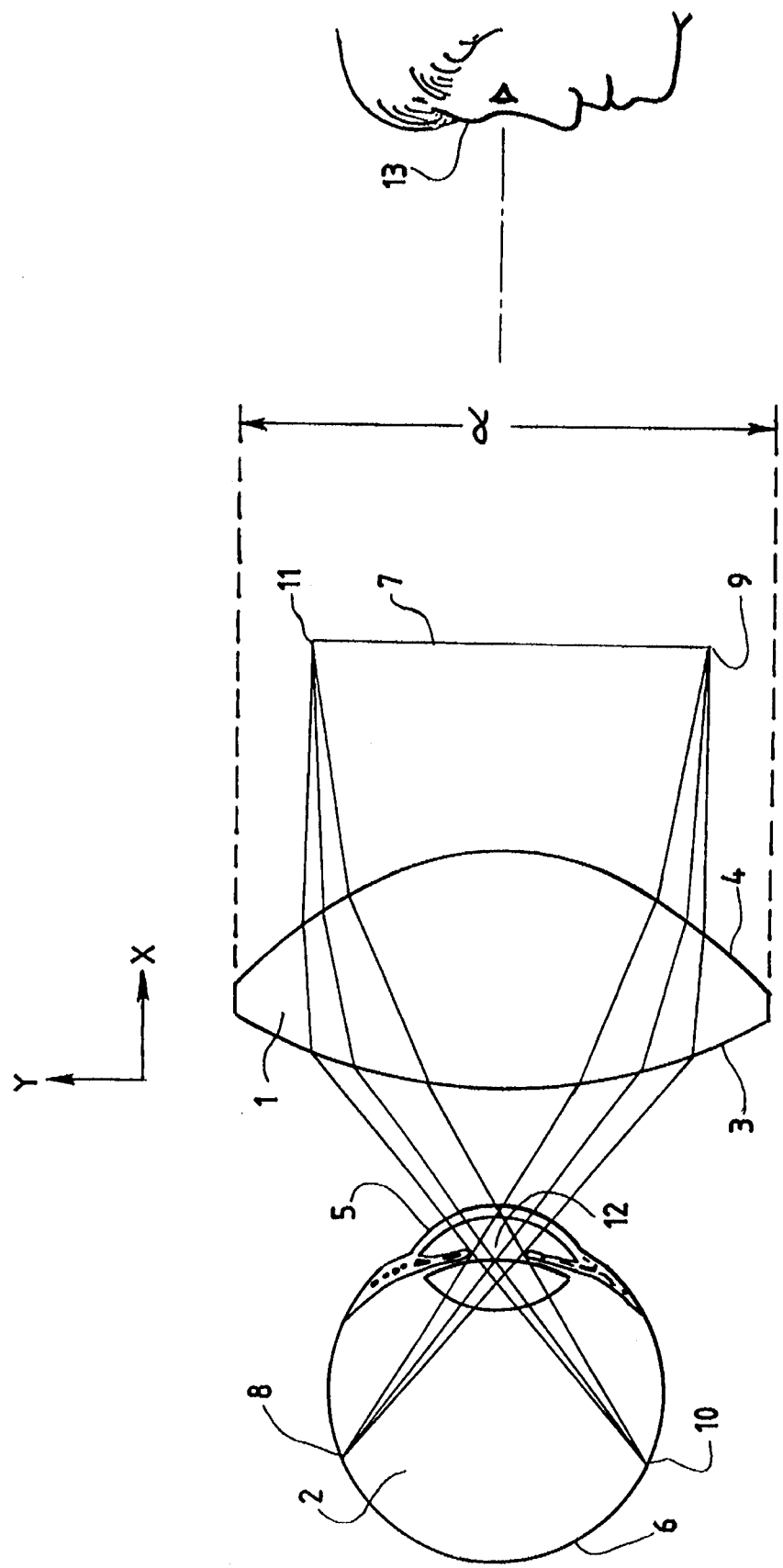

LENS FOR OBSERVATION OF THE INTERIOR OF THE EYE

TECHNICAL FIELD

This invention relates to a fundus observation lens which provides a means for examination of the interior of an eye and more particularly to a lens for observing a wide field of view image of the fundus of an eye through an undilated pupil.

BACKGROUND OF THE INVENTION

A common procedure performed by ophthalmologists is the examination of the interior of a patient's eye. This is an important procedure since variations in the appearance of the interior of a patient's eye can give an ophthalmologist important information on the health of a patient or the proliferation of a number of ocular diseases.

Commonly in an examination procedure, the ophthalmologist applies a topical drug to the patients eye to dilate the pupil of the eye. Using a known condensing lens which the ophthalmologist holds in close proximity to the patient's eye in conjunction with an illumination system, the ophthalmologist is able to observe the interior of the patient's eye. Examples of various types of condensing lenses are disclosed in the following U.S. Pat. Nos.: 4,738,521; 4,682,866; 4,627,694; 4,721,378; 4,728,183; 5,007,729; 3,954,329; and 4,469,413. These condensing lenses in general produce images that are useful to the ophthalmologist conducting the examination. The patient, however, must endure the various side effects of the dilation drug such as blurry vision, light hypersensitivity and poor depth perception. These side effects may persist up to several hours following an examination.

SUMMARY OF THE INVENTION

In accordance with the present invention the disadvantages of prior lenses used to observe the fundus of a patient's eye have been overcome. The fundus observation lens of the present invention is a nonsymmetric lens with two curved, nonspherical surfaces specifically shaped to capture the image rays from the fundus exiting the small undilated pupil of the patient's eye to form a wide field of view, real inverted image of the interior of the eye having minimal distortions.

More particularly, the lens of the present invention is formed of an optically transparent material having a first curved surface to be positioned adjacent to the eye of a patient and a second curved surface opposite said first surface. Each of said first surface and said second surface has a shape described by the polynomial function:

$$x = f(Y, A_2, A_4, A_6, C, cc) = A_2Y^2 + A_4Y^4 + A_6Y^6 + CY^2/(1 + \sqrt{1 - C^2ccY^2})$$

where the curvature C for the first surface is greater than $-\frac{1}{2}$ times the curvature C for the second surface.

The image produced by the lens of the present invention has a field of view greater than 30° and in a preferred embodiment greater than 60°. Further, the ratio of the effective focal length of the lens to the diameter of the lens is less than 0.5 with magnification on the order of 0.7×.

These and other objects, advantages and novel features of the present invention, as well as details of an illustrative embodiment thereof, will be more fully understood from the following description and the drawing.

BRIEF DESCRIPTION OF THE DRAWING

FIG. 1 is a cross-sectional schematic view of the lens of the present invention shown in close proximity to a patient's eye.

DESCRIPTION OF THE PREFERRED EMBODIMENT

A lens 1 in accordance with the present invention is positioned in close proximity to the patient's eye 2. The lens 1 is formed of an optically transparent material and has a first surface 3 that is positioned facing the patient's eye 2, adjacent to the cornea 5 and a second lens surface 4 that faces the observing ophthalmologist 13. The optically transparent material may be glass or a plastic such as polymethylmethacrylate or other suitably transparent optical material.

A light source, not shown, illuminates the fundus of the eye so as to produce light rays, such as the peripheral bundles of light rays 8, 10, emanating from the fundus 6 of the eye 2. The rays diverge from the fundus and pass through the undilated pupil of the eye 12, which is the limiting aperture of the eye. The rays exit the eye at the cornea 5 and are captured by the first surface 3 of the lens 1. The first surface 3 of the lens 1 directs the rays 8, 10 emanating from the undilated eye 2 towards the second lens surface 4 which focuses the rays 8, 10 to respective points 9, 11 so as to form a planar, inverted real image 7 of the fundus 6. The ophthalmologist is able to observe the image 7 of the interior of the eye using, for example, an indirect ophthalmoscope, a refractingscope or even merely a pen light or the like forming the light source illuminating the eye.

In order to use the lens 1 with an undilated eye, each surface of the lens is preferably described by the polynomial function:

$$f(Y, A_2, A_4, A_6, C, cc) = A_2Y^2 + A_4Y^4 + A_6Y^6 + CY^2/(1 + \sqrt{1 - C^2ccY^2})$$

where $A_2$, $A_4$ and $A_6$ are constants; C represents the curvature of the surface; and cc represents the conic constant. For the first surface 3 of the lens 1, these values should be within the following ranges:

0.003<A2<0.0

0.0<A4<0.001

−0.001<A6<0.001

0.03<C<0.06

−2.0<cc<0.0

For the second surface 4 of the lens 1, these values should be within the following ranges:

0.0<A2<0.003

−0.02<A4<0.02

−0.01<A6<0.01

−0.1<C<0.0

−2.0<cc<1.0

Further, the curvature C of the first surface 3 should be greater than $-\frac{1}{2}$ times the curvature C of the second surface 4.

In a preferred embodiment of the lens 1 the first surface 3 of the lens 1, has the values of: A2=−0.00243, A4=0.0000012, A6=0.0, C=0.045 and cc=−1.213; whereas the second surface 4 of the lens 1, has values of: A2=0.000444, A4=−0.000001, A6=0.0, C=−0.092 and cc=−0.933.

While the diameter, d, of the lens may be varied, the preferred diameter is 35 millimeters. This diameter in conjunction with the preferred values for the first surface 3, enables the lens 1 to capture the peripheral fundus image rays 8, 10 which would miss the edge of lens surface 3 if it were too strongly curved.

The magnification of the planar real inverted image, Im, may be described by the equation:

$$Im=FLln/FLne$$

where FLne is 17.06 millimeters, the approximate, effective focal length of a normal emmetropic eye and FLln is the effective focal length of the lens 1 as measured from the vertex of the second surface 4 towards the ophthalmologist 13. In the preferred embodiment, the focal length FLln is approximately 12.3 millimeters. Therefore, the magnification of the real inverted image is approximately 0.7×. For the preferred embodiment, the ratio of the effective focal length of the lens 1 to the diameter of the lens 1 is approximately 0.35. However, in accordance with the present invention the ratio of the effective focal length of the lens 1 to the diameter of the lens 1 can be as great as 0.5.

The lens 1 of the present invention produces a greater than 30° field of view real image of a patient's fundus without the need for dilation of the patients pupil, thus allowing the ophthalmologist to perform the necessary diagnostic procedures without the normal uncomfortable side effects for the patient. Further in accordance with the preferred embodiment a field of view of approximately 65° is obtained so that a large area of the patient's fundus 6 is observable without the need to dilate the patient's eye. The planar real image produced by the lens of the present invention is further substantially free of distortions.

Many modifications and variations of the present invention are possible in light of the above teachings. Thus, it is to be understood that, within the scope of the appended claims, the invention may be practiced otherwise than as described hereinabove.

What is claimed and desired to be secured by Letters Patent is:

1. A lens for observing the interior of an eye through an undilated pupil comprising an optically transparent material having a first curved surface to be positioned facing the eye to be observed and a second curved surface opposite said first surface, each of said first and second surfaces having a shape described by a polynomial function $$f(Y, A_2, A_4, A_6, C, cc) =$$

$$A_2Y^2 + A_4Y^4 + A_6Y^6 + CY^2/(1 + \sqrt{1 - C^2ccY^2}\ )$$

where $-0.003 < A2 < 0.0$, $0.0 < A4 < 0.001$, $-0.001 < A6 < 0.001$, $0.03 < C < 0.06$, and $-2.0 < cc < 0.0$ for said first surface; $0.0 < A2 < 0.003$, $-0.02 < A4 < 0.02$, $-0.01 < A6 < 0.01$, $-0.1 < C < 0.0$, and $-2.0 < cc < 1.0$ for said second surface and the curvature, C, of the first surface is greater than −½ times the curvature, C, of the said second surface.

2. A lens for observing the interior of an eye as recited in claim 1, said lens producing a real inverted image of the eye's fundus with a magnification of approximately 0.7×.

3. A lens for observing the interior of an eye as recited in claim 1 wherein A2 is approximately equal to −0.00243, A4 is approximately equal to 0.0000012, A6 is approximately equal to 0.0, C is approximately equal to 0.045 and cc is approximately equal to −1.213 for said first surface and A2 is approximately equal to 0.000444, A4 is approximately equal to −0.000001, A6 is approximately equal to 0.0, C is approximately equal to −0.092 and cc is approximately equal to −0.933.

4. A lens for observing the interior of an eye as recited in claim 1 wherein said lens has a diameter of approximately 35 millimeters and produces a real image of the eye's fundus with a magnification of 0.7×.

5. A lens for observing the interior of an eye through an undilated pupil comprising: an optically transparent material having a first curved surface to be positioned facing the eye to be observed and a second curved surface opposite said first surface, said first surface having a curvature sufficient to bend rays emanating from the eye's fundus through an undilated pupil of the eye towards the second surface and said second surface having sufficient curvature to form said rays into a real inverted image of a patient's fundus, each of said first and second surfaces having a shape described by a polynomial function $$f(Y, A_2, A_4, A_6, C, cc) =$$

$$A_2Y^2 + A_4Y^4 + A_6Y^6 + CY^2/(1 + \sqrt{1 - C^2ccY^2}\ )$$

where the curvature C of said first surface is greater than −½ times the curvature C of said second surface.

6. A lens for observing the interior of an eye as recited in claim 5, said lens producing a real inverted image of the eye's fundus with a magnification of approximately 0.7×.

7. A lens for observing the interior of an eye as recited in claim 5 wherein the diameter of said lens is approximately 35 millimeters and produces a real image of the eye's fundus with a magnification of 0.7×.

8. A nonsymmetric lens for observing the interior of an eye through an undilated pupil comprising: an optically transparent material having a first curved surface to be positioned facing the eye to be observed and a second curved surface opposite said first surface, said first surface having a curvature sufficient to bend rays emanating from the eye's fundus through an undilated pupil towards the second surface and said second surface having sufficient curvature to form said rays into a real inverted image of the patient's fundus with a field of view that is greater than 30°, said lens having an effective focal length and a diameter such that the ratio of the effective focal length to the lens diameter is less than 0.5.

9. A lens for observing the interior of an eye as recited in claim 8 wherein at least one of said surfaces has a shape described by a polynomial function $$f(Y, A_2, A_4, A_6, C, cc) =$$

$$A_2Y^2 + A_4Y^4 + A_6Y^6 + CY^2/(1 + \sqrt{1 - C^2ccY^2}\ )$$

10. A lens for observing the interior of an eye as recited in claim 9 where said first surface has the shape described by said polynomial function and $-0.003 < A2 < 0.0$, $0.0 < A4 < 0.001$, $-0.001 < A6 < 0.001$, $0.03 < C < 0.06$, and $-2.0 < cc < 0.0$.

11. A lens for observing the interior of an eye as recited in claim 9 where said second surface has the shape described by said polynomial function and $0.0 < A2 < 0.003$, $-0.02 < A4 < 0.02$, $-0.01 < A6 < 0.01$, $-0.1 < C < 0.0$, and $-2.0 < cc < 1.0$.

12. A lens for observing the interior of an eye as recited in claim 8 wherein said field of view is greater than 60°.

13. A lens for observing the interior of an eye as recited in claim 8 having a magnification of at least 0.7×.

* * * * *